(12) United States Patent
Lee et al.

(10) Patent No.: US 6,861,162 B2
(45) Date of Patent: Mar. 1, 2005

(54) ORGANIC ELECTROLUMINESCENCE DEVICES USING PYRAZOLO[3,4B] QUINOXALINE DERIVATIVES

(75) Inventors: Shuit-Tong Lee, Hong Kong (CN); Chun-Sing Lee, Hong Kong (CN); Peng-Fei Wang, Hong Kong (CN); Zhi-Yuan Xie, Hong Kong (CN)

(73) Assignee: CityU Research Ltd., Hong Kong (CN)

( * ) Notice: Subject to any disclaimer, the term of this patent is extended or adjusted under 35 U.S.C. 154(b) by 96 days.

(21) Appl. No.: 10/229,493

(22) Filed: Aug. 28, 2002

(65) Prior Publication Data

US 2004/0043247 A1 Mar. 4, 2004

(51) Int. Cl.$^7$ .............................................. H05B 33/12
(52) U.S. Cl. ...................... 428/690; 428/917; 313/504; 313/506
(58) Field of Search ................................ 428/690, 917; 313/504, 506

(56) References Cited

U.S. PATENT DOCUMENTS 5,281,489 A * 1/1994 Mori et al. .................. 428/690
5,935,720 A   8/1999 Chen et al. ................. 428/690

OTHER PUBLICATIONS

Pengfei Wang et al., "New 1H–pyrazolo[3,4–b]quinoxaline derivatives . . . electroluminescent devices", Chem. Commun., vol. 13, pp. 1404–1405 (first published as an Advance Article on Web May 29, 2002).*
Derwent–Acc–No: 1986–183553 and ZCAPLUS 1986:626652; both for DD 234014, Mar, 1986.*
J.L. Segura, "The Chemistry of Electroluminescent Organic Materials," *Acta Polym.* 49, 319–44 (1998), no month.
C.W. Tang and S.A. Van Slyke, "Organic Electroluminescent Diodes," *Appl. Phys. Lett.*, 51 (12), 913–15 (Sep. 1987).
L. Hennig et al., "Oxidative Kupplung von 5–Amino–pyrazolen mit p–Phenylendiaminen," *J. f. prakt. Chemie.* 328, 342–48 (1986), no month.
Z. Kucybala et al., "Development of New Dyeing Photoinitiators for Free Radical Polymerization based on the 1H–Pyrazolo[3,4–b]Quinoxaline Skeleton. Part 2," *J. Chem. Soc., Perkin Trans. 2* 1559–67 (published on Web Jun. 2000).
Z. Kucybala et al., "Development of New Dyeing Photoinitiators for Free Radical Polymerization based on 3–Methyl–1–Phenyl–1H–Pentaazacyclopenta[b]naphthalene Skeleton III," *J. Photochemistry and Photobiology A: Chemistry* 136, 227–34 (2000), no month.
C.H. Chen et al., "Recent Developments in Molecular Organic Electroluminescent Materials," *Macromol. Symp.* 125, 1–48 (1997), no month.
U.Mitschke and P. Bäuerle, "The Electroluminescence of Organic Materials," *J. Mater. Chem.* 10, 1471–1507 (published on Web Jun. 2000).
Y. Shirota, "Organic Materials for Electronic and Optoelectronic Devices," *J. Mater. Chem.* 10, 1–25 (2000), no month.

* cited by examiner

*Primary Examiner*—Marie Yamnitzky
(74) *Attorney, Agent, or Firm*—Heslin Rothenberg Farley & Mesiti P.C.

(57) ABSTRACT

An organic electroluminescence device which includes an anode, a cathode, a hole transport layer, an electron transport layer, and at least one organic luminescent medium doped with a pyrazolo[3,4b]quinoxaline derivative is disclosed. The present device provides improved efficiency, and the emission band associated therewith is surprisingly narrow. The improved green emitting organic electroluminescence device exhibits high color purity.

3 Claims, 2 Drawing Sheets

ORGANIC ELECTROLUMINESCENCE DEVICES USING PYRAZOLO[3,4B] QUINOXALINE DERIVATIVES

FIELD OF THE INVENTION

This invention relates to an organic electroluminescence (EL) device and, more particularly, to the use of novel pyrazolo[3,4b]quinoxaline derivatives for thin-film type organic electroluminescence devices.

BACKGROUND OF THE INVENTION

In the 1960s, many trials for the preparation of an organic electroluminescence device were reported by using conjugated materials generally having a fused aromatic ring (U.S. Pat. No. 3,172,862, issued 1965; U.S. Pat. No. 3,173,050, issued 1965). The efficiencies and lifetimes of these organic EL devices were much lower than those obtained from inorganic systems at the same time, so research mainly focused on the inorganic materials. The reason for the low luminance of the early organic EL device is the highly resistive EL medium, which prevents the efficient injection of carriers into the light-emitting layer. Tang and VanSlyke solved this problem successfully in the late 1980s (Tang and VanSlyke, Appl. Phys. Lett. 1987, 51, 913). They improved the performance of an organic EL device significantly by using a structure made of two thin layers: a hole transporting layer of an organic substance laminated on an organic emitting layer. This work revived the research on organic EL devices, and resulted in the development of a new generation of light-emitting diodes with organic dyes. Since then, much work has been done to further improve the efficiency, stability, color purity and so forth of such a device. (U.S. Pat. Nos. 5,141,671; 4,539,507; 6,020,078; 5,935,720; 5,972,247; 5,593,788; 4,885,211; 5,059,862; 5,104,740; 5,069,975; 5,126,214; 5,389,444; 6,165,383; 6,245,449; Chen, Shi and Tang, Macromol. Symp., 1997, 125, 1; Segura, Acta. Polym., 1998, 49, 319; Mitschke and Bauerle, J. Mater. Chem. 2000, 10, 1471). Among these, one of the most convenient and useful methods is to dope a strong emitting material into a host material to form a guest-host system. Thus, in principle, an organic EL device with good efficiency and high stability, as well as desired color with proper chromaticity, can be obtained by doping different strongly emitting materials into a host material, such as tri-(8-hydroxyquinolinato)aluminum ($AlQ_3$), to meet the requirement of the practical applications. As a general rule, the energy gap between the lowest unoccupied molecular orbital (LUMO) and the highest occupied molecular orbital (HOMO) of a host material should be larger than that of the doped guest material to allow an efficient energy transfer from the host to guest.

$AlQ_3$ is one of the most useful host materials in organic EL devices. It has been used as the host material for a green-emitting device (Shi and Tang, U.S. Pat. No. 5,593,788), as well as a red-emitting device made of 4-(dicyanomethylene)-2-methyl-6-(p-dimethylaminostyryl)-4H-pyran (DCM) derivatives (Chen, Tang and Shi, U.S. Pat. No. 5,935,720). As for the guest materials that emit at longer wavelengths, such as green, yellow and red regions, two kinds of compounds are potential candidates: (i) compounds with large fused homo-aromatic rings; and (ii) intramolecular charge transfer (ICT) compounds with electron donating (D) groups and electron withdrawing (A) groups linked by conjugated structure. Since the fused homo-aromatic compounds with large conjugated structures, especially those that emit in the red, are often oxidized easily by singlet oxygen at ambient conditions, these compounds are not expected to be suitable dopants unless the devices are used in the dark or without oxygen. Compared with the former compounds, ICT compounds have the following advantages:

(i) The emission wavelength can be easily tuned by changing substituents to get different colors;

(ii) The molecular structure is relatively easy to modify for desired properties;

(iii) Their Stokes shifts are generally large to prevent efficient self-re-absorption; especially in the solid state; and (iv) They are chemically stable, not easily oxidized by singlet oxygen.

Pyrazolo[3,4b]quinoxaline derivatives have been used as photo-initiators (Kucybala et al., J. Photochem. Photobiol., A, 2000, 136(3), 227; Perkin 2, 2000, 7, 1559) and as antibacterial agents. The preparation of some 7-dimethylamino, diethylamino substituted pyrazolo[3,4b] quinoxaline derivatives was reported in the 1980s (Mann et al., J. Prakt. Chem., 1986, 328(3), 342). On the other hand, these materials have not been used in organic EL devices. The pyrazolo[3,4b]quinoxaline derivatives in the present invention are typical ICT compounds, so these compounds are expected to have the general features of ICT compounds mentioned above. The compounds disclosed herein exhibit a very high fluorescence and a narrow emission band, as indicated in FIG. 2. Thus, it is desirable to use these pyrazolo[3,4b]quinoxaline derivatives as emitting materials to achieve organic electroluminescence devices with improved efficiency and color purity.

SUMMARY OF THE INVENTION

The object of the present invention is to provide an organic electroluminescence device comprising an anode, a cathode, a hole transport layer, an electron transport layer, and at least one organic emitting layer containing a compound of formula (I) or (II):

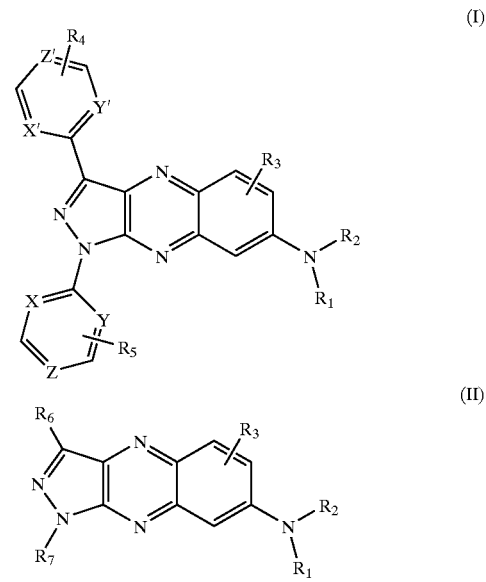

In structures (I) and (II), each X, Y, Z, X', Y', and Z' is independently carbon (C) or nitrogen (N), and each $R_1$-$R_7$ is selected independently from the groups consisting of hydrogen, halogen, cyano, nitro, carbonyl, sulfone, ester, alkyl, alkoxy, alkyl, alkyl amino, dialkylamino, aryl amino, diarylamino, haloalkyl containing a lower alkyl, hydroxyalkyl containing a lower alkyl, styryl, alkyloxy, alkylthio, aryloxy, arylthio, siloxy, aryl or substituted aryl, and substituted or unsubstituted heterocyclic hydrocarbons.

This invention also provides a novel organic electroluminescence device with an unexpectedly improved efficiency and narrow emission band. For example, when one of the pyrazolo[3,4b]quinoxaline derivatives having formula [I] or [II] is doped into $AlQ_3$, it gives a green emission of the CIE x, y chromaticity similar to that of undoped $AlQ_3$. Surprisingly, though, its emission peak width is only 60% of that of $AlQ_3$, as shown in FIG. 2. This surprising feature of the present invention provides for an improved green emitting organic electroluminescence device with exceptionally high color purity and efficiency. Furthermore, the materials used in the invention are easy to prepare, and thus are economically attractive.

DETAILED DESCRIPTION OF THE PREFERRED EMBODIMENTS

Figure 1:
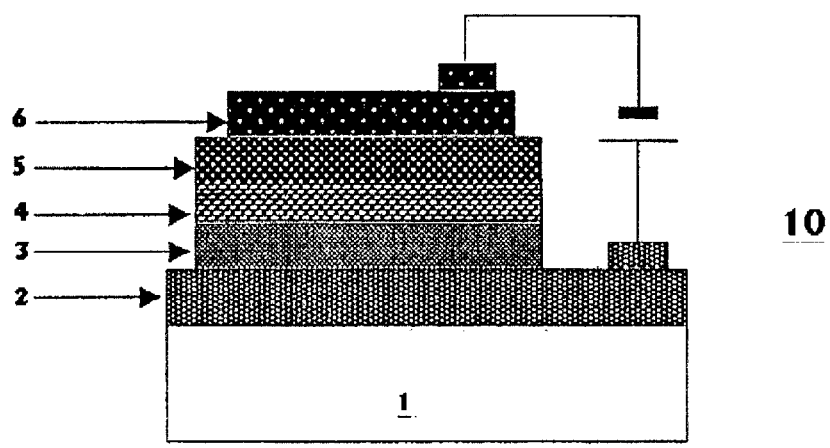
FIG. 1 is a diagram showing the structure of the organic electroluminescence device of the present invention.

FIG. 1 illustrates a diagram of the organic electroluminescence device structure 10. Reference numeral 1 indicates a substrate; numeral 2 indicates an anode; numeral 3 indicates an organic hole transport layer; numeral 4 indicates an organic emitting layer; numeral 5 indicates an organic electron transport layer; numeral 6, indicates a cathode.

The substrate 1 is used as a support for the organic electroluminescence device of the present invention. A suitable substrate is, for example, a quartz or glass sheet, a metal sheet or foil, or a plastic film or sheet. The preferred material for use in the device is a glass sheet, or a transparent synthetic resin, such as a polyester, polycarbonate, or polysulfone.

An anode 2 is located on the substrate 1. It is usually made of a metal such as silver, gold, aluminum, nickel, palladium, a metal oxide such as an oxide of indium and/or tin, e.g., indium tin oxide (ITO), carbon black, or a conductive resin such as poly(3-methylthiophene). The materials mentioned above for making anode 2 may also be employed in preparing cathode 6. However, the preferred material for cathode 6 is a metal with low work function, which is conducive to the efficient injection of electrons. Thus, a suitable metal such as magnesium, aluminum, silver, indium, or their alloys may be used.

Methods for preparing anode 2 and cathode 6 generally include vacuum deposition and sputtering. However, when the material comprises fine particles of a metal, carbon black, a metal oxide, or conductive resin powder, it can be dispersed into a suitable binder resin in solution and coated on a substrate to form the electrodes. Furthermore, in the case of a conductive resin, a thin film may be formed directly on a substrate by electrolytic polymerization.

Anode 2 and/or cathode 6 can be made to have a multilayered structure by depositing layers of the different materials mentioned above. However, at least one of the electrodes should transmit visible light to a required degree: usually at least 60%, but preferably at least 80%. In this respect, the layer should not be too thick, generally from 5–1,000 nm, and preferably from 10–500 nm.

An organic hole-transport layer 3 is located on anode 2. It generally comprises a compound that is able to transport holes (i.e. positive charge carriers) efficiently from anode 2 to the organic emitting layer 4 between the electrodes to which an electric field is applied (external power source not shown). Such a compound must be highly efficient at injecting holes from the anode. In addition, the compound must be capable of efficiently transporting the injected holes to an emitting material found in emitting layer 4, thereby preventing the migration of excitons generated in emitting layer 4 from an electron injecting zone or an electron transporting material. The material should also be highly capable of forming a thin film. Thus, in this respect, a suitable hole-transporting compound usually has a low ionization potential, large hole mobility and stability. Moreover, the impurities likely to form traps should not be produced during preparation or use.

Materials known to be useful as hole transporting materials, either combined or separately, include those disclosed in U.S. Pat. No. 5,935,720, phthalocyanine derivatives, naphthalocyanine derivatives, porphyrin derivatives, pyrazoline derivatives, carbazole derivatives, benzidine type triphenylamine, diamine type triphenylamine, derivatives of these, and polymeric materials such as polyvinylcarbazole, polysilane.

In the organic electroluminescence device 10 of the present invention, effective hole transporting materials preferably include an aromatic tertiary amine derivative. Exemplary suitable hole-transporting materials are fully described by Y. Shirota in *J. Mater. Chem.* 10, 1–25 (2000) and are illustrated as follows:

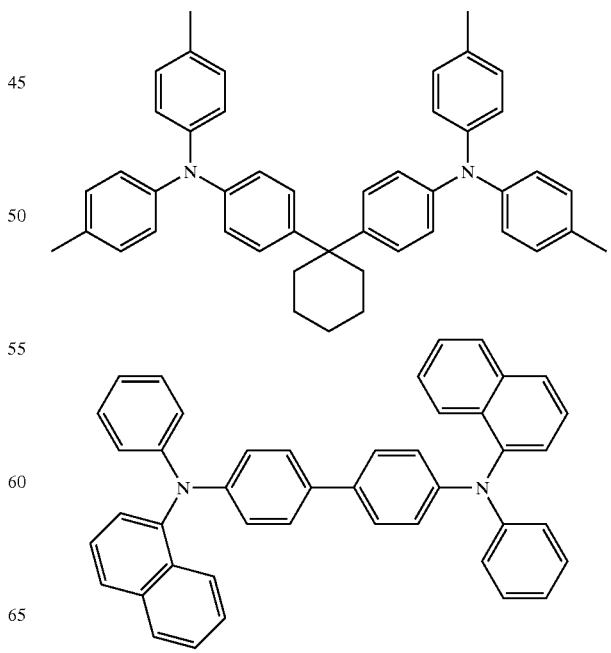

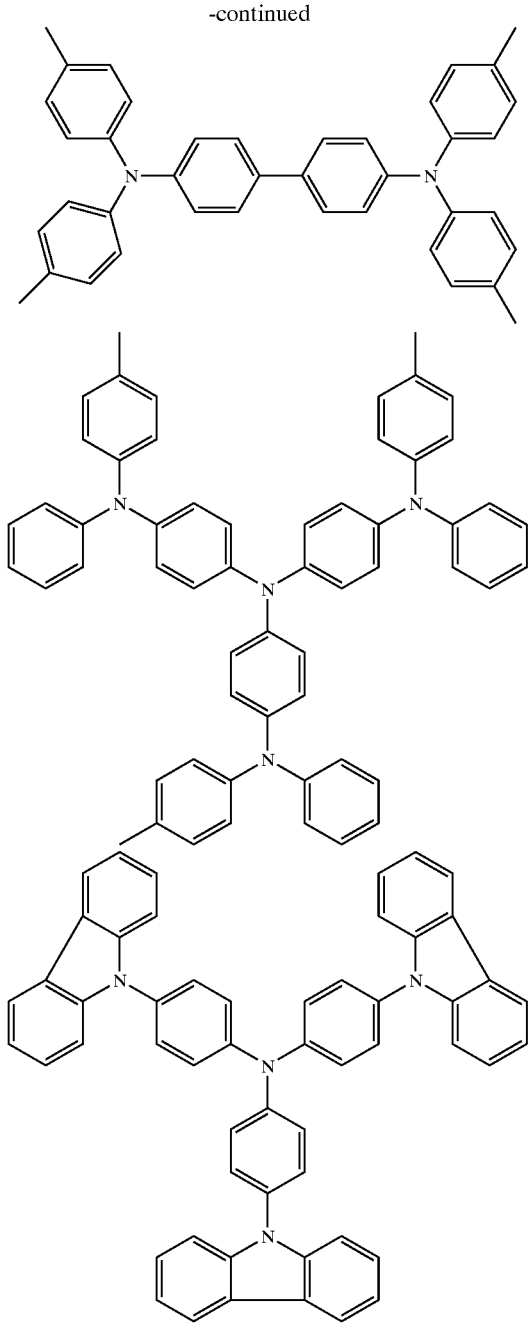

derivatives, perylene tetracarboxylic acid derivatives, oxadiazole derivatives, metal complexes of 8-hydroxyquinoline, 10-hydroxybenzo[h]quinoline, pyrrolopyridine derivatives, naphthylidine derivatives. Several examples, which are also disclosed by Y. Shirota in *J. Mater. Chem.* 10, 1–25 (2000), are shown as follows:

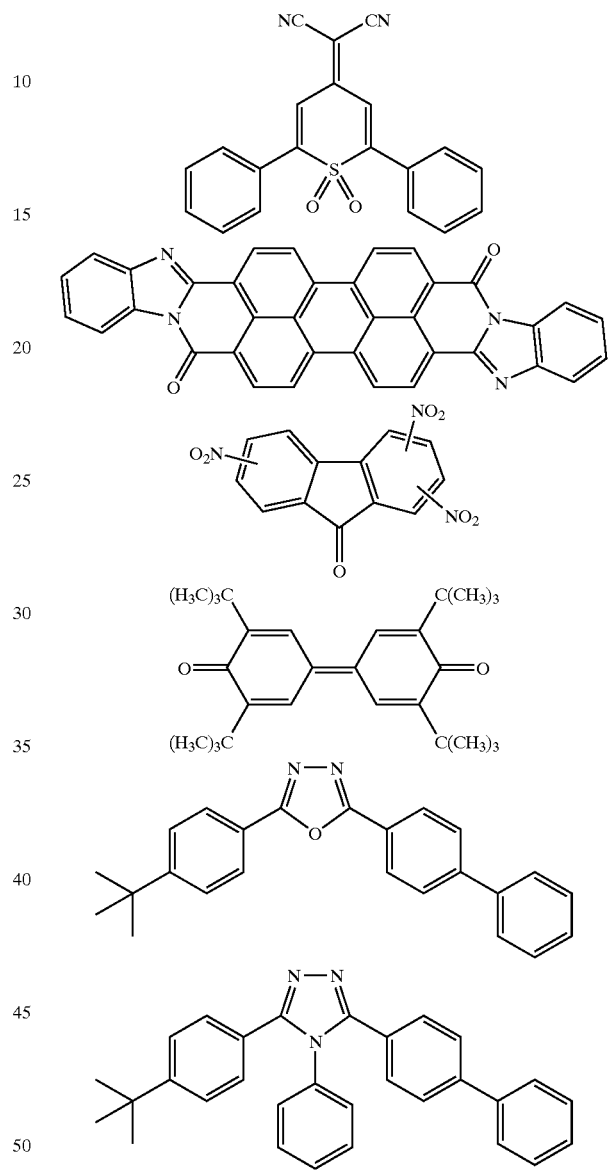

The hole transporting material can be laminated on anode 2 by a vacuum deposition method or a coating/casting method to form organic hole transport layer 3 in the present invention. This hole transport layer usually has a thickness of from 5–400 nm, preferably from 30–100 nm. In order to obtain a thin film uniformly, the vacuum deposition method is preferred.

The organic electron transport layer 5 should be a material into which electrons from cathode 6 can be injected easily, which has excellent electron transport mobility, and which blocks the migration of excitons generated in the light-emitting layer 4 into the hole injection zone. Moreover, a material which has a good ability to form a thin film is desirable.

Useful electron transport materials generally have a large electron affinity, such as, for example, thiopyrandioxide Electron transport layer 5 can be formed by a vacuum deposition method or a coating/casting method. This electron transport layer 5 usually has a thickness of from 5–400 nm, preferably from 30–100 nm. In order to obtain a thin film uniformly, vacuum deposition is preferred.

The organic light-emitting layer 4 of the present invention comprises a light emitting material wherein electroluminescence is produced as a result of electron-hole recombination in this region. This electron-hole recombination produces excitons, which may decay to the ground state in a radiative way, resulting in an emission—fluorescence or phosphorescence. The light emitting material is generally required to have a high emission quantum yield, a suitable energy gap, as well as a good ability to form a thin film uniformly. Materials for the emitting material include fused aromatic compounds, benzidine type triphenylamine, styrylamine type triphenylamine, diamine type triphenylamine, 8-hydroxyquinolinato metal complexes, such as $AlQ_3$, as well as other fluorescence or phosphorescence dyes.

As previously mentioned, doping a strong luminescent material into one of the light emitting materials (host) mentioned above can significantly improve the performance of an organic EL device. This method is believed to have the following advantages:

(i) Electroluminescent efficiency may be improved significantly
(ii) Color can be tuned by doping different emitting materials
(iii) Emitting materials with poor ability to form film and with concentration self-quenching can also be used.
(iv) The stability of an organic EL device can be improved.

Accordingly, in the present invention, organic light-emitting layer 4 comprises a multi-component material containing a host emitting material, such as one of those listed above, and a dopant (guest). It should be noted that the multi-component material of layer 4 may also include a hole transport material or an electron transport material, such as those described herein, as required.

Of the light emitting materials listed above, the well-known emitting material, ($AlQ_3$), is particularly suitable for use as the host in the present organic light-emitting layer 4. However, it should be noted that the EL device of the present invention is not limited to the use of $AlQ_3$, and other hosts, such as those listed above, may be used instead.

As for the dopants, the above-disclosed pyrazolo[3,4b] quinoxaline compounds with formula [I] or [II] have surprisingly proved to be highly capable at improving the efficiency and the hue of light emission. In formula [I], X, Y, Z, X', Y', and Z' are each independently carbon or nitrogen. In formulae [I] and [II], each $R_1$–$R_7$ is independently hydrogen, halogen, cyano, nitro, carbonyl, sulfone, ester, alkoxy, alkyl, alkyl amino, dialkylamino, aryl amino, diarylamino, haloalkyl containing a lower alkyl, hydroxyalkyl containing a lower alkyl, styryl, alkyloxy, alkylthio, aryloxy, arylthio, siloxy, aryl, substituted aryl, heterocyclic hydrocarbons, and substituted heterocyclic hydrocarbons.

"Alkyl" refers to saturated hydrocarbon residues containing eighteen or fewer carbons in straight or branched chains, as well as cyclic structures. "Lower alkyl" refers to those containing from 1 to 4 carbon atoms. "Aryl" means an aromatic hydrocarbon of 4 to about 16 carbon atoms. The term "heterocyclic hydrocarbon" means an unsaturated cyclic residue with 1 to 6 carbon atoms and 1 to 4 heteroatoms chosen from the group consisting of nitrogen, oxygen and sulfur.

Examples of suitable alkyl groups containing from 1–18 carbon atoms include methyl, ethyl, propyl, butyl, sec-butyl, tert-butyl, pentyl, hexyl, heptyl, octyl, stearyl, and the like. Examples of alkyl amino residues include methyl amino, ethyl amino, propyl amino, butyl amino, sec-butyl amino, tert-butyl amino, pentyl amino, hexyl amino, heptyl amino, octyl amino, stearyl amino, and the like. Examples of dialkylamino groups include dimethyl amino, diethyl amino, dipropyl amino, dibutyl amino, disec-butyl amino, ditert-butyl amino, dipentyl amino, dihexyl amino, diheptyl amino, dioctyl amino, distearyl amino, and the like. Phenyl amino is an exemplary arylamino. Examples of diarylamino groups include diphenyl amino, phenylnaphthylamino, phenylanthrylamino, o-, p-, m-tolylnaphthylamino, o-, p-, m-tolylanthrylamino, naphthylanthrylamino, and the like. Examples of lower "haloalkyl" groups include chloromethyl, 3-chloropropyl, dichloromethyl, trichloromethyl, fluoromethyl, difluoromethyl, trifluoromethyl, and the like. Lower "hydroxyalkyl" radicals include hydroxymethyl, hydroxyethyl, and the like. "Alkyloxy" groups, also referred to as alkoxyl", include methoxy, ethoxy, propoxy, butoxy, sec-butoxy, tert-butoxy, stearyloxy, and the like. Phenoxy is an example of an "aryloxy" residue. Examples of "alkylthio" substituents include methylthio, ethylthio, propylthio, butylthio, sec-butylthio, tert-butylthio, and the like. Phenylthio is an example of an "arylthio" group. Examples of substituted or unsubstituted "aryl" groups containing only monocyclic hydrocarbons include phenyl, biphenyl, triphenyl, tert-phenyl, o, m-, p-tolyl, xylyl. o-, m-, p-cumyl, mesityl, and the like. Exemplary fused polycyclic aryl groups, substituted or unsubstituted, include pentarhenyl, indenyl, naphthyl, azulenyl, heptalenyl, acenaphthylenyl, phenalenyl, fluorenyl, anthryl, anthraquinonyl, phenanthrolyl, pyrenyl, chrysenyl, picenyl, rebicenyl, trinaphthylenyl, and the like. "Heterocyclic hydrocarbons", substituted or unsubstituted, include pyranthrenyl, oparenyl, thienyl, furyl, pyrrolyl, imidazolyl, pyrazolyl, pyridyl, pyrazinyl, pyrimidinyl, pyridazinyl, indolyl, quinolyl, isoquinolyl, phthalazinyl, quinoxalinyl, quinazolinyl, carbazolyl, acrydinyl, phenadinyl, furfuryl, isoxiazolyl, isothiazolyl, isoquinazolyl, furazanyl, phenoquisadinyl, benzothiazolyl, benzoxazolyl, benzimidazolyl, and the like.

Molecular structures for exemplary dopants useful in the present invention are as follows:

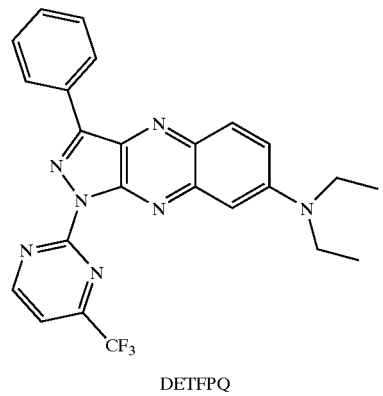

DETFPQ

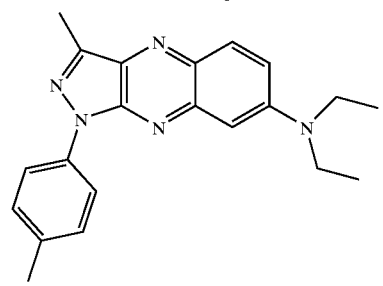

DETMPQ

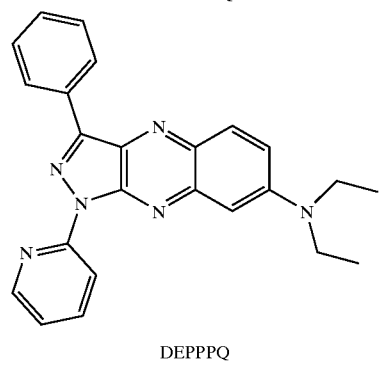

DEPPPQ

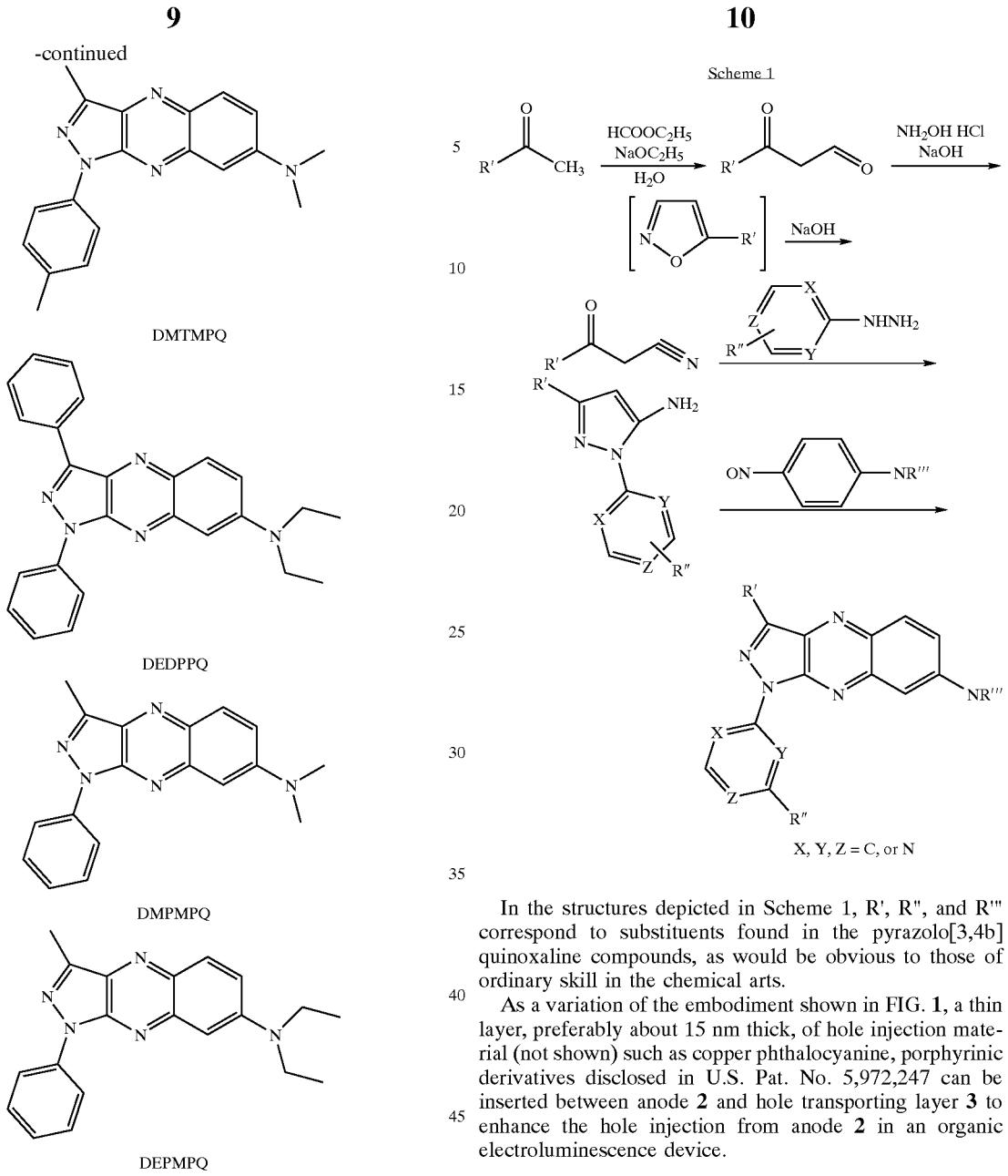

DETFPQ, DEPPPQ, and DEDPPQ are examples of pyrazolo[3,4b]quinoxaline compounds having formula [I], and DETMPQ, DMTMPQ, DMPMPQ, and DEPMPQ are examples having formula [II]. When formula [I] is DETFPQ, X and Y are each nitrogen; Z, X', Y', and Z' are each carbon; $R_1$ and $R_2$ are each ethyl; $R_3$ and $R_4$ are each hydrogen; and $R_5$ is trifluoromethyl. In DEPPPQ X is nitrogen; Y, Z, X', Y', and Z' are each carbon; $R_1$ and $R_2$ are each ethyl; and $R_3$, $R_4$, and $R_5$ are each hydrogen. In DEDPPQ, X, Y, Z, X', Y', and Z' are all carbon atoms; $R_1$ and $R_2$ are each ethyl; and $R_3$, $R_4$, and $R_5$ are each hydrogen. With respect to the formula [II] examples, in DETMPQ, $R_1$ and $R_2$ are each ethyl; $R_3$ is hydrogen; $R_6$ is methyl; and $R_7$ is p-tolyl. In DMTMPQ, $R_1$ and $R_2$ are each methyl; $R_3$ is hydrogen; $R_6$ is methyl; and $R_7$ is p-tolyl. In DMPMPQ, $R_1$ and $R_2$ are each methyl; $R_3$ is hydrogen; $R_6$ is methyl; and $R_7$ is phenyl. In DEPMPQ, $R_1$ and $R_2$ are each ethyl; $R_3$ is hydrogen; $R_6$ is methyl; and $R_7$ is phenyl.

The pyrazoloquinoxaline derivatives can be synthesized as shown in Scheme 1.

In the structures depicted in Scheme 1, R', R", and R'" correspond to substituents found in the pyrazolo[3,4b] quinoxaline compounds, as would be obvious to those of ordinary skill in the chemical arts.

As a variation of the embodiment shown in FIG. 1, a thin layer, preferably about 15 nm thick, of hole injection material (not shown) such as copper phthalocyanine, porphyrinic derivatives disclosed in U.S. Pat. No. 5,972,247 can be inserted between anode 2 and hole transporting layer 3 to enhance the hole injection from anode 2 in an organic electroluminescence device.

EXAMPLES

The present invention will be explained in more detail with reference to examples hereinafter. It should be noted that the examples included below are for illustrative purposes only, and that the invention is in no way limited to the embodiments used in the examples.

Unless otherwise indicated, the reactants and reagents used in the reactions described below are readily available materials. Such materials can be conveniently prepared in accordance with conventional preparatory procedures or obtained from commercial sources.

Example 1
Synthesis of the Sodium Salt of Benzoylacetaldehyde

To 500 ml dry ether was added 30 g acetophenone and 20 g ethylformate followed by 15 g sodium methoxide. The mixture was stirred for 24 hrs at room temperature. The precipitate was collected by filtration, washed with ether, and dried under vacuum to get 30 g sodium salt of benzoylacetaldehyde.

Example 2
Synthesis of Benzoylacetonitrile

To a solution of 10 g sodium salt of benzoylacetaldehyde (prepared according to the procedure of Example 1) and 10 g hydroxyamine chloride in 30 ml ethanol was added 20 ml 50% NaOH at 0–10° C. The mixture was then refluxed for 24 hrs, and concentrated to 2/3 volume. The brown solution was neutralized with the concentrated hydrochloric acid. The precipitate was collected by filtration, and dried under vacuum to get a solid with slight pink color, 3.8 g benzoylacetonitrile.

Example 3
Synthesis of 1,3-diphenyl-5-aminopyrazole

To a solution of 1.08 g hydrazine in 10 ml 5N hydrochloric acid was added 1.45 g benzoylacetonitrile (prepared according to the procedure of Example 2), under stirring. The mixture was refluxed for 3 hrs. After cooling, the solution was neutralized with $Na_2CO_3$. The yellow precipitate was filtrated, washed with $H_2O$, and dried to get 2.1 g 1,3-diphenyl-5-aminopyrazole.

Example 4
Synthesis of 1-(2-pyridyl)-3-phenyl-5-aminopyrazole

To a solution of 1.09 g 2-hydrazinopyridine in 10 ml 5N hydrochloric acid was added 1.45 g benzoylacetonitrile (from Example 2) under stirring. The mixture was refluxed for 3 hrs. After cooling, the solution was neutralized with $Na_2CO_3$. The yellow precipitate was filtrated, washed with $H_2O$, and dried to get 1.9 g 1-pyridyl-3-phenyl-5-aminopyrazole.

Example 5
Synthesis of 1-(3-trifluoromethyl-2,6-pyrimidine)-3-phenyl-5-aminopyrazole To a solution of 1.78 g 2-hydrazino-4-(trifluoromethyl) pyrimidine in 10 ml 5N hydrochloric acid was added 1.45 g benzoylacetonitrile (from Example 2) under stirring. The mixture was refluxed for 3 hrs. After cooling, the solution was neutralized with $Na_2CO_3$. The yellow precipitate was filtrated, washed with $H_2O$, and dried to get 2.4 g 1-(3-trifluoromethyl-2,6-pyrimidine)-3-phenyl-5-aminopyrazole.

Syntheses of Pyrazolo[3,4]quinoxaline Derivatives

Example 6
Synthesis of 7-diethylamino-1,3-diphenyl-1H-pyrazolo[3,4-b]quinoxaline(DEDPPQ)

1.78 g N,N-diethyl-p-nitrosoaniline and 2.65 g 1,3-diphenyl-5-aminopyrazole were refluxed for 2 hrs in acetic acid. The mixture was concentrated to half volume. Water was added to get a precipitate, then filtered. The solid was purified by chromatograph column on silica gel. After removing the solvent, 1.6 g pure 7-diethylamino-1,3-diphenyl-1H-pyrazolo[3,4-b]quinoxaline (DEDPPQ) was obtained as a brown solid.

Example 7
Synthesis of 7-diethylamino-3-phenyl-1-(2-pyridyl)-1H-pyrazolo[3,4-b]quinoxaline(DEPPPQ)

1.78 g N,N-diethyl-p-nitrosoaniline and 2.67 g 3-phenyl-1-(2-pyridyl)-5-aminopyrazole were refluxed for 2 hrs in acetic acid. The mixture was concentrated to half volume. Water was added to get a precipitate, then filtered. The solid was purified by chromatograph column on silica gel. After removing the solvent, 1.3 g pure 7-diethylamino-3-phenyl-1-(2-pyridyl)-1H-pyrazolo[3,4-b]quinoxaline (DEPPPQ) was obtained as brown-red solid.

Example 8
Synthesis of 7-diethylamino-3-phenyl-1-(3-trifluoromethyl-2,6-pyrimidine)-1H-pyrazolo[3,4-b]quinoxaline (DETFPQ)

1.78 g N,N-diethyl-p-nitrosoaniline and 3.55 g 1-(3-trifluoromethyl-2,6-pyrimidine)-3-phenyl-5-aminopyrazole (prepared according to the procedure of Example 5) were refluxed for 2 hrs in acetic acid. The mixture was concentrated to half volume. Water was added to get precipitate, then filtered. The solid was purified by chromatograph column on silica gel. After removing the solvent, 1.8 g pure 7-diethylamino-3-phenyl-1-(3-trifluoromethyl-2,6-pyrimidine)-1H-pyrazolo[3,4-b]quinoxaline (DETFPQ) was obtained as deep brown solid.

Example 9
Synthesis of 7-diethylamino-1-(p-tolyl)-3-methyl-1H-pyrazolo[3,4-b]quinoxaline (DETMPQ)

1.78 g N,N-diethyl-p-nitrosoaniline and 2.03 g 1-(p-tolyl)-3-methyl-5-aminopyrazole were refluxed for 2 hrs in acetic acid. The mixture was concentrated to half volume. Water was added to get precipitate, then filtered. The solid was purified by chromatograph column on silica gel. After removing the solvent, 1.5 g pure 7-diethylamino-1-(p-tolyl)-3-methyl-1H-pyrazolo[3,4-b]quinoxaline(DETMPQ) was obtained as yellow-brown solid.

Example 10
Synthesis of 7-dimethylamino-1-(p-tolyl)-3-methyl-1H-pyrazolo[3,4-b]quinoxaline (DMTMPQ)

1.50 g N,N-dimethyl-p-nitrosoaniline and 2.03 g 1-(p-tolyl)-3-methyl-5-aminopyrazole were refluxed for 2 hrs in acetic acid. The mixture was concentrated to half volume. Water was added to get precipitate, then filtered. The solid was purified by chromatograph column on silica gel. After removing the solvent, 1.5 g pure 7-dimethylamino-1-(p-tolyl)-3-methyl-1H-pyrazolo[3,4-b]quinoxaline (DMTMPQ) was obtained as brown solid.

Example 11
Synthesis of 7-dimethylamino-1-phenyl-3-methyl-1H-pyrazolo[3,4-b]quinoxaline (DMPMPQ)

1.50 g N,N-dimethyl-p-nitrosoaniline and 1.89 g 1-phenyl-3-methyl-5-aminopyrazole were refluxed for 2 hrs in acetic acid. The mixture was concentrated to half volume. Water was added to get precipitate, then filtered. The solid was purified by chromatograph column on silica gel. After removing the solvent, 1.2 g pure 7-dimethylamino-1-phenyl-3-methyl-1H-pyrazolo[3,4-b]quinoxaline (DMPMPQ) was obtained as yellow-brown solid.

Example 12
Synthesis of 7-diethylamino-1-phenyl-3-methyl-1H-pyrazolo[3,4-b]quinoxaline (DEPMPQ)

1.78 g N,N-diethyl-p-nitrosoaniline and 1.89 g 1-phenyl-3-methyl-5-aminopyrazole were refluxed for 2 hrs in acetic acid. The mixture was concentrated to half volume. Water was added to get precipitate, then filtered. The solid was purified by chromatograph column on silica gel. After removing the solvent, 1.6 g pure 7-diethylamino-1-phenyl-3-methyl-1H-pyrazolo[3,4-b]quinoxaline(DEPMPQ) was obtained as brown solid.

Electroluminescence Device Fabrication

The detailed results of electroluminescence are indicated in the following specific examples of the present invention. It is evident that the light emitting efficiency and the hue of light emission can be improved by doping the materials of the present invention into a host material.

Example 13

An indium-tin-dioxide (ITO) coated glass substrate 1 was sequentially ultrasonicated in a detergent, rinsed in deionized water and exposed to UV light for 20 minutes, and dried. A hole transporting layer 3 of N,N'-bis-(1-naphthyl)-N,N'-diphenylbenzidine was deposited on ITO anode 2 at the vacuum deposition rate of about 15 nm/min. by using a tantalum boat to form a thickness of 60 nm. A light-emitting layer 4 of $AlQ_3$ doped with a material having formula [I] or [II] was then co-deposited onto the hole-transporting layer 3 with a thickness of about 30 nm. The concentration of dopants can be controlled by deposition rate as required. In the following step, an electron-transporting layer 5 of $AlQ_3$ was deposited onto the light-emitting layer 4 with a thickness of about 30 nm. Then, a cathode 6 consisting of a 10/1 atomic ratio of Mg/Ag was deposited onto the $AlQ_3$ layer 5 with a thickness of about 200 nm. Finally, the device was hermetically packaged in a dry glove box.

Example 14

Figure 2:
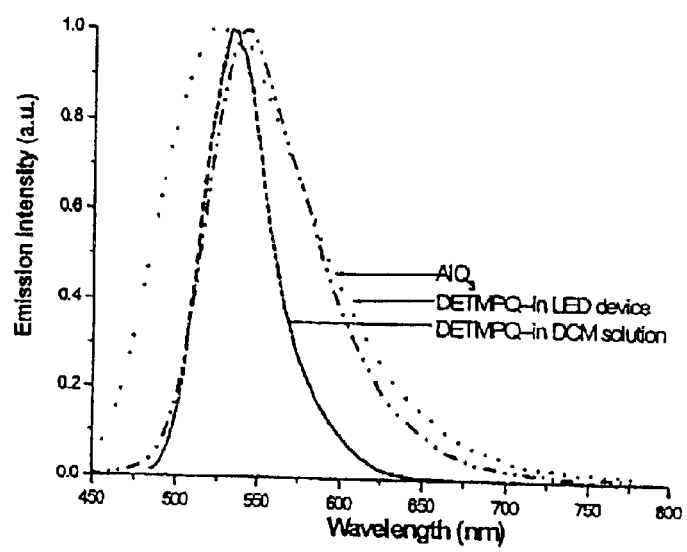
FIG. 2 is a plot of Emission Intensity vs. Wavelength, which shows the fluorescent spectra of $AlQ_3$ emitting materials doped with a pyrazolo[3,4b]quinoxaline derivative, in accordance with the present invention, and the spectrum of undoped $AlQ_3$.

The electroluminescence device with 7-diethylamino-1-(p-tolyl)-3-methyl-1H-pyrazolo[3,4-b]quinoxaline (DETMPQ) (from Example 9) doped $AlQ_3$ as the light-emitting layer was fabricated by following the procedure of Example 13. The light emission characteristics were found as follows: a luminescence of $1460(cd/m^2)$ at $20\ mA/m^2$, a bias voltage of 6.2 volts with a luminescence efficiency of 7.44 (cd/A); a green emission from the doped emitting material with CIE coordinates x, y=0.33, 0.61. FIG. 2 compares the fluorescent spectrum of undoped $AlQ_3$ with the spectra of the emitting material in the EL device described in this example, and with (DEPMPQ)(Example 12) doped $AlQ_3$ in dichloromethane solution (DCM). The graph shows the very high fluorescence of DETMPQ doped $AlQ_3$ and the associated narrow emission bands relative to undoped $AlQ_3$.

Example 15

The electroluminescence device with 7-dimethylamino-1-(p-tolyl)-3-methyl-1H-pyrazolo[3,4-b]quinoxaline (DMTMPQ) (Example 10) doped $AlQ_3$ as the light-emitting layer was fabricated by following the procedure of Example 13. The light emission characteristics were found as follows: a luminescence of $1600(cd/m^2)$ at $20\ mA/m^2$, a bias voltage of 6.2 volts; with a luminescence efficiency of 7.62 (cd/A); a green emission from the doped emitting material with CIE coordinates x, y=0.36, 0.60.

Example 16

The electroluminescence device with 7-diethylamino-3-phenyl-1-(3-trifluoromethyl-2,6-pyrimidine)-1H-pyrazolo[3,4-b]quinoxaline(DETFPQ)(Example 8) doped $AlQ_3$ as the light-emitting layer was fabricated by following the same procedure as in Example 13. The light emission characteristics were found as follows: a luminescence of $1400(cd/m^2)$ at $20\ mA/m^2$, a bias voltage of 6.2 volts; with a luminescence efficiency of 7.94 (cd/A); a green emission from the doped emitting material with CIE coordinates x, y=0.43, 0.56.

Example 17

The electroluminescence device with 7-diethylamino-3-phenyl-1-pyridyl-1H-pyrazolo[3,4-b]quinoxaline (DEPPPQ)(Example 7) doped $AlQ_3$ as the light-emitting layer was fabricated by following the procedure of Example 13. The light emission characteristics were found as follows: a luminescence of $1815(cd/m^2)$ at $20\ mA/m^2$, a bias voltage of 6.2 volts; with a luminescence efficiency of 8.99 (cd/A); a green emission from the doped emitting material with CIE coordinates x, y=0.37, 0.59.

Example 18

The electroluminescence device with 7-dimethylamino-1-phenyl-3-methyl-1H-pyrazolo[3,4-b]quinoxaline (DMPMPQ) (Example 11) doped $AlQ_3$ as the light-emitting layer was fabricated by following the procedure of Example 13. The light emission characteristics were found as follows: a luminescence of $1700(cd/m^2)$ at $20\ mA/m^2$, a bias voltage of 6.2 volts; with a luminescence efficiency of 7.9 (cd/A); a green emission from the doped emitting material with CIE coordinates x, y=0.34, 0.60.

Example 19

The electroluminescence device with 7-diethylamino-1-phenyl-3-methyl-1H-pyrazolo[3,4-b]quinoxaline (DEPMPQ)(Example 12) doped $AlQ_3$ as the light-emitting layer was fabricated by following the procedure of Example 13. The light emission characteristics were found as follows: a luminescence of $2010(cd/m^2)$ at $20\ mA/m^2$, a bias voltage of 6.2 volts; with a luminescence efficiency of 9.65 (cd/A); a green emission from the doped emitting material with CIE coordinates x, y=0.36, 0.59.

Example 20

The electroluminescence device with 7-diethylamino-1,3-diphenyl-1H-pyrazolo[3,4-b]quinoxaline (DEDPPQ) (Example 6) doped $AlQ_3$ as the light-emitting layer was fabricated by following the procedure of Example 13. The light emission characteristics were found as follows: a luminescence of $1540(cd/m^2)$ at $20\ mA/m^2$, a bias voltage of 6.2 volts; with a luminescence efficiency of 7.52 (cd/A); a green emission from the doped emitting material with CIE coordinates x, y=0.37, 0.57.

Table 1 shows spectral, photophysical and electroluminescent data from the examples of the present invention.

TABLE 1

Spectral, Photophysical and Electroluminescent Data of Compounds at Room Temperature

| Compounds | | Solvents $E_T(30)$ (Kcal/mol) | $DCM^a$ 41.1 | $EL^b$ | C.I.E. (x, y) | Efficiency (Cd/A) |
|---|---|---|---|---|---|---|
| DEPPPQ | $\lambda^{ab.}_{max}(nm)$ | | 469 | 544 | 0.37, 0.57 | 7.5 |
| | $\epsilon(dm^3mol^{-1}\ cm^{-1})$ | | 14980 | | | |
| | $\lambda^{em.}_{max}(nm)$ | | 538 | | | |
| | $\Phi_f^c$ | | 0.95 | | | |
| DETFPPQ | $\lambda^{ab.}_{max}(nm)$ | | 467 | 544 | 0.37, 0.59 | 9.0 |
| | $\epsilon(dm^3mol^{-1}\ cm^{-1})$ | | 15950 | | | |
| | $\lambda^{em.}_{max}(nm)$ | | 538 | | | |
| | $\Phi_f^c$ | | 0.95 | | | |
| DEDPPQ | $\lambda^{ab.}_{max}(nm)$ | | 468 | 552 | 0.43, 0.56 | 7.9 |
| | $\epsilon(dm^3mol^{-1}\ cm^{-1})$ | | 15930 | | | |
| | $\lambda^{em.}_{max}(nm)$ | | 538 | | | |
| | $\Phi_f^c$ | | 0.94 | | | |
| DEPMPQ | $\lambda^{ab.}_{max}(nm)$ | | 457 | 540 | 0.36, 0.59 | 9.7 |
| | $\epsilon(dm^3mol^{-1}\ cm^{-1})$ | | 15930 | | | |
| | $\lambda^{em.}_{max}(nm)$ | | 538 | | | |
| | $\Phi_f^c$ | | ~1 | | | |
| DMPMPQ | $\lambda^{ab.}_{max}(nm)$ | | 451 | 540 | 0.34, 0.60 | 7.9 |
| | $\epsilon(dm^3mol^{-1}\ cm^{-1})$ | | 14980 | | | |
| | $\lambda^{em.}_{max}(nm)$ | | 529 | | | |
| | $\Phi_f^c$ | | ~1 | | | |
| DETMPQ | $\lambda^{ab.}_{max}(nm)$ | | 456 | 536 | 0.33, 0.61 | 7.4 |
| | $\epsilon(dm^3mol^{-1}\ cm^{-1})$ | | 15650 | | | |
| | $\lambda^{em.}_{max}(nm)$ | | 532 | | | |
| | $\Phi_f^c$ | | ~1 | | | |
| DMTMPQ | $\lambda^{ab.}_{max}(nm)$ | | 446 | 540 | 036, 0.60 | 7.6 |
| | $\epsilon(dm^3mol^{-1}\ cm^{-1})$ | | 15950 | | | |
| | $\lambda^{em.}_{max}(nm)$ | | 525 | | | |
| | $\Phi_f^c$ | | 0.95 | | | |

[a]DMC = dichloromethane,
[b]EL = electroluminescence,
[c]Fluorescence quantum yield ($\Phi_f$) were measured by using rhodamine B in ethanol as the Standard ($\Phi_f = 0.70$).

As indicated in Table 1, the emission maximum is located between 530–550 nm, i.e., green color, although the maximum emission can be shifted either to the red or to the blue by changing the intramolecular charge transfer (ICT). Furthermore, all compounds show the extremely high fluorescence quantum yield up to almost unity because of their unique structures.

Each of the patents and other references cited herein is incorporated by reference herein in its entirety.

Herein we have described the specific embodiments of the present invention; further modifications and improvements will occur to those skilled in the art. We desire it to be understood, therefore, that this invention is not limited to the particular forms shown and we intend in the appended claims to cover all modifications that do not depart from the spirit and scope of this invention.

We claim:

1. An organic electroluminescence device comprising an anode, a hole transport layer adjacent said anode, at least one organic emitting layer adjacent said hole transport layer, an electron transport layer adjacent said at least one organic emitting layer, and a cathode adjacent said electron transport layer, wherein said at least one organic emitting layer contains a compound of the formula [I]

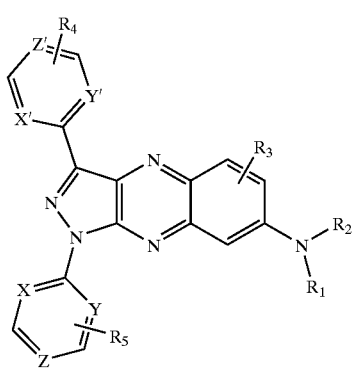

(I)

wherein X is N atom each Y, Z, X', Y', and Z' is independently a C or N atom, and each $R_1$–$R_5$ is selected independently from the groups consisting of hydrogen, halogen, cyano, nitro, carbonyl, sulfone, ester, alkoxy, alkyl, alkyl amino, dialkylamino, aryl amino, diarylamino, haloalkyl containing a lower alkyl, hydroxyalkyl containing a lower alkyl, styryl, alkyloxy, alkylthio, aryloxy, arylthio, siloxy, aryl, substituted aryl, heterocyclic hydrocarbon, and substituted heterocyclic hydrocarbon.

2. The organic electroluminescence device of claim 1, further comprising a layer of hole injection material between said anode and said hole transport layer.

3. The organic electroluminescence device of claim 1, wherein said compound of formula [I] is selected from the group consisting of DETFPQ, and DEPPPQ:

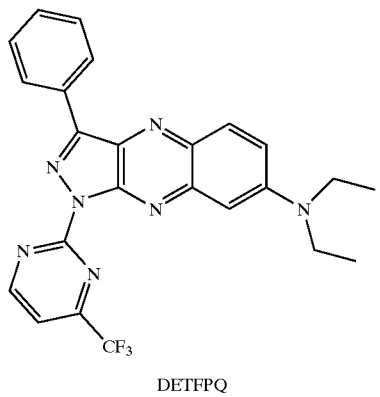

DETFPQ

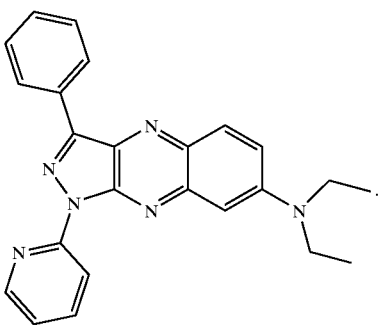

DEPPPQ

* * * * *